United States Patent [19]

Sharvit et al.

[11] Patent Number: 4,810,797

[45] Date of Patent: Mar. 7, 1989

[54] METHOD OF PREPARING 2,3,6-TRICHLOROPYRIDINE AND 2,3,5,6-TETRACHLOROPYRIDINE IN THE GAS PHASE

[75] Inventors: Joseph Sharvit; David Lubetzky; Abraham A. Pereferkovich, all of Beer Sheva, Israel

[73] Assignee: Makhteshim Chemical Works Ltd., Beer Sheva, Israel

[21] Appl. No.: 32,437

[22] Filed: Mar. 30, 1987

[30] Foreign Application Priority Data

Mar. 31, 1986 [IL] Israel ........................................ 78341

[51] Int. Cl.$^4$ ............................................ C07D 213/61
[52] U.S. Cl. ............................................ 546/345
[58] Field of Search ................................ 546/345

[56] References Cited

U.S. PATENT DOCUMENTS 1,977,662  10/1934  Wibaut et al. ...................... 546/345
3,899,495   8/1975  Beschke et al. .................... 546/345
4,281,135   7/1981  Perettie et al. ..................... 546/345

FOREIGN PATENT DOCUMENTS 78410    5/1983  European Pat. Off. ............ 546/345
1545984  4/1970  Fed. Rep. of Germany ...... 546/345

OTHER PUBLICATIONS

Patent Abstracts of Japan, vol. 8, No. 46 (C-212) (1483), Feb. 29, 1984.
Chemical Abstracts, 100: 138966j (1984) (Japan, Kokai JP 58,206,564, 12/1/83).

Primary Examiner—Richard A. Schwartz
Attorney, Agent, or Firm—Browdy and Neimark

[57] ABSTRACT 2,3,6-Trichloropyridine and 2,3,5,6-tetrachloropyridine are prepared by continuously reacting chlorine in the gas phase with one or more compounds such as 2,6-dichloropyridine and 2,3,6-trichloropyridine at a temperature of from about 200° C. in the presence of an amount of catalyst effective to catalyze the reaction.

40 Claims, No Drawings

METHOD OF PREPARING 2,3,6-TRICHLOROPYRIDINE AND 2,3,5,6-TETRACHLOROPYRIDINE IN THE GAS PHASE

FIELD OF THE INVENTION

The present invention concerns an improved process for preparing chlorinated pyridines having at least three chloro substituents. The present invention particularly concerns the preparation of 2,3,6-trichloropyridine, and 2,3,5,6-tetrachloropyridine.

BACKGROUND OF THE INVENTION

The chlorinated pyridine derivatives of the present invention are known compounds, having been previously prepared by a number of known processes, and are also employed as chemical intermediates in the preparation of other highly desired herbicide or pesticide products. Previous methods for preparing such compounds include those described in U.S. Pat. Nos. 3,538,100 and 3,186,994 and the prior art noted therein. Thus U.S. Pat. No. 3,538,100 describes the preparation of 2,3,5,6-tetrachloropyridine and pentachloropyridine by chlorination of liquid 2,6-dichloropyridine at a temperature of at least 180° C. and in the presence of a metallic halide catalyst. However, reaction times of 45–90 hours are required. U.S. Pat. No. 3,186,994 describes the preparation 2,3,5,6-tetrachloropyridine and pentachloropyridine by chlorinating, in the absence of a catalyst, a polychloro-(trichloromethyl)-pyridine reactant in the liquid state. However, the preferred reactions require either irradiation with ultraviolet light or temperatures above 400° C.

U.S. Pat. No. 3,420,833 describes a process for preparing polychlorinated pyridines by chlorinating pyridine in the gas phase in the absence of a catalyst. However, as shown in comparative examples 29–33 hereinafter, the process described therein results in the predominant formation of 2,3,4,5,6-pentachloropyridine or the formation of pentachloropyridine with significant amounts of undesirable 2,4,6-trichloropyridine and/or 2,3,4,6-tetrachloropyridine co-product.

U.S. Pat. No. 3,370,062 describes the preparation of pentachloropyridine by chlorinating in the gas phase a mixture of pyridine, methylpyridines, and chloropyridines in the presence of catalysts such as silica or alumina. However, this reaction also results in the predominant formation of 2,3,4,5,6 pentachloropyridine and affords a yield of less than fifty percent. In addition, this reaction was not adaptable to form 2,3,5,6-tetrachloropyridine.

U.S. Pat. No. 3,555,032 describes a continuous process for preparing 2,3,4,5-tetrachloropyridine by chlorinating 2-chlorpyridine hydrochloride in the liquid phase. However, a reaction time of at least an hour and preferably 60 to 40 hours is needed, and this process does not yield the highly desirable 2,3,5,6-tetrachloropyridine.

U.S. Pat. No. 4,256,894 describes a process for preparing polychloropyridines by chlorinating chloro-substituted (trichloromethyl) pyridine in the liquid phase in the presence of a Lewis acid type catalyst. However, this process requires high pressure and a reaction time of 18–24 hours while affording a mixture of products.

U.S. Pat. No. 4,281,135 describes a process for preparing 2,3,5,6-tetrachloropyridine and pentachloropyridine by chlorinating 2,6-dichloropyridine in the liquid phase in the presence of an oxide catalyst. However, this reaction must be run under pressure with a reaction time of 11–30 hours.

Recently DE No. 3,306,905 reported the continuous preparation of pentachloropyridine by the gas phase chlorination of pyridine in the presence of coke as a catalyst. However, this process requires a fluidized bed reactor at a temperature of 550° C.

SUMMARY OF THE INVENTION

With this state of the art in mind, it is an object of the present invention to provide a new and improved method for the production of the commercially needed 2,3,6-trichloropyridine and 2,3,5,6-tetrachloropyridine. It is a further object of the present invention to provide a method, more economical than known methods, for the production of 2,3,5,6-tetrachloropyridine substantially free of tarry by-products and in high yields. An additional object is the provision of a method which gives the desirable and high yields of the 2,3,5,6-tetrachloropyridine in a very short period of time. A further object is the provision of a method which affords high yields of the specifically desired polychlorinated pyridines by simple variation of the conditions of the reaction.

In accordance with the present invention there is now provided a process for the selective chlorination of a polychlorinated pyridine chosen from the group consisting of 2,6-dichloropyridine and 2,3,6-trichloropyridine comprising continuously reacting chlorine in the gas phase with at least one of said halopyridines at a temperature of at least about 200° C. and in the presence of a catalyst selected from the group consisting of silicates, silicate clays, mineral earths, pumice, zeolites, diatomaceous earths, carborundum, or mixtures thereof, said diatomaceous earths or carborundum containing an additive selected from the group consisting of activated carbon, iron, zinc, aluminum or a Lewis acid halide, whereby 2,6-dichloropyridine is selectively chlorinated to predominantly form 2,3,6-trichloropyridine, 2,3,5,6-tetrachloropyridine or mixtures thereof, and 2,3,6-trichloropyridine is selectively chlorinated to predominantly form 2,3,5,6-tetrachloropyridine.

Thus the present invention enables the selective and predominant production of 2,3,6-trichloropyridine and 2,3,5,6-tetrachloropyridine, in amounts in excess of 50% and preferably in amounts in excess of 80% and this especially when the reaction is conducted at a preferred temperature of about 200° C. to about 500° C.

In preferred embodoiments of the present invention said silicate, silicate clay, mineral earth, pumice or zeolite catalyst are used in combination with an additive selected from the group consisting of activated carbon, iron, zinc or a Lewis acid halide.

The process of the present invention can be conducted to provide mixtures of different chlorinated pyridines, which can be readily separated; or to provide optimum amounts of the highly desired 2,3,5,6-tetrachloropyridine, while minimizing the production of the other polychloropyridine products. The process of the present invention is preferably conducted under anhydrous conditions and atmospheric pressure; and is most preferably carried out to produce the preferred product of symmetrical tetrachloropyridine.

DETAILED DESCRIPTION OF THE INVENTION

In carrying out the process of the present invention, chlorine and 2,6-dichloropyridine, 2,3,6-trichloropyridine, or a mixture of 2,6-dichloropyridine and 2,3,6-trichloropyridine are reacted at a temperature of at least about 200° C. in the presence of a selected catalyst. The most suitable rate at which the chlorine gas is fed will vary with the reaction temperature, type of catalyst, and end-product desired.

The process of the present invention may be carried out by reacting equimolar amounts of chlorine and the halopyridine starting material. However, the reaction is then relatively long. For economic reasons it is preferred to shorten the reaction time by using an excess of chlorine. While an excess of 20 to 100 percent can be used, it is preferred to use an excess of 25 to 50 percent.

The process of the present invention may be carried out with or without an inert solvent. Examples of such solvents inert to the conditions of the reaction of the present invention are halogenated hydrocarbons, as carbon tetrachloride. Good results are obtained when the reactions of the present invention are run containing 1 to 99 preferably 2 to 20% of the chloropyridine reactant. However, it is most preferred to run the reactions containing no solvent.

While a lower limit of about 200° C. is required for the present reactions, the preferred temperature will depend upon the starting material, the type of catalyst used, the residence time, and the end-product desired. As a general rule the shorter the residence time, the higher temperature required. However, a temperature of about 500° C. should be considered as the upper limit; for at this temperature the chloropyridine reactants begin to rapidly form undesired products such as 2,4,6-trichloropyridine, 2,3,4,6-tetrachloropyridine, and pentachloropyridine.

The residence time of the reactions of the present invention will naturally depend upon the starting material, the temperature, the type of catalyst used, and the end-product desired. However, residence time of 0.1 to 20 seconds and preferably 0.5 to 6 seconds are usually employed.

A catalyst is required in order to obtain 2,3,6,trichloropyridine and the highly desired 2,3,5,6-tetrachloropyridine by chlorination of 2,6-dichloropyridine, 2,3,6-trichloropyridine or a mixture of 2,6-dichloropyridine and 2,3,6-trichloropyridine. Included among the satisfactory catalysts which may be employed are silicates, like vermiculite, talc, and pyrophyllite; silicate clays or mineral earths from the montmorrilloniod group as bentonites, saponites, hectories, or illites; the kaolinite group as kaolin or halloysite; or the attapulgite group as attapulgite or sepiolite; zeolites, or pumice.

Representative forms of these clays and earths which can catalyze the reactions of the present invention include Diluex, a trade name for attapulgite from the Floridin Co., Tallahassee, Fla.; Attaclay, a trade name for attapulgite from Engelhard minerals, N.J.; Pyrax B, a trade name for pyrophyllite from R. T. Vanderbilt Co., N.Y.; Dicalite-408, a trade name for pyrophyllite from Dicalite Co., N.Y.; Volclay-200, a trade name for bentonite from American Colloid Co., Chicago, Ill.; and Suprex Clay, a trade name for kaolin from J. M. Huber Corp., N.Y. Further details on these earths are available in the following publication: *Handbook of Insecticide Dust Diluents and Carriers,* by T. C. Watkins and C. B. Norton, 2nd Edition revised and ddited by D. E. Weidhaas and J. L. Brann, Jr., Orland Books, Caldwell, N.J., 1955.

While these catalysts are effective when used alone, they are also effective when mixtures of them are used. A representative form of such a mixture is pyrophyllite and bentonite. Weight ratios of 1:10 to 1:5 are effective, with a weight ratio of between 1:9 to 1:7 particularly effective.

The effectiveness of the above catalysts is enhanced when they have incorporated into them additives such as activated carbon or Lewis acid halides. The Lewis acid halides may be in the form of the chloride; for example, ferric chloride, aluminum chloride, zinc chloride, copper chloride, and the like. They may also be incorporated as the free metal or metal oxide, which form a Lewis acid halide under the conditions of the reaction. Examples of these are free iron, zinc, or aluminum and ferric oxide. These enhancers may be incorporated into the above catalysts in weight ratios of from 1 to 25 preferably 1 to 15, percent. Examples of these are carbon on attapulgite, ferric chloride on bentonite, ferric chloride on a pyrophyllite-bentonite mixture.

A further satisfactory class of catalyst which may be employed are diatamaceous earths or carborundum containing one of the above mentioned additives.

These mixtures are uniformly prepared by mixing the dry ingredients until a homogenized powder is obtained, adding water while mixing until granuals are formed, drying the granuals, and passing the dry mixture through a sieve, retaining those particles of 2-5 mm.

A preferred class of catalysts are the silicate clay materials or mineral earths. Highly preferred catalysts for use in the present invention include attapulgite, activated carbon on attapulgite, kaolin, and ferric chloride in a pyrophyllite-bentonite mixture.

While the prior art noted herein teaches that 2,6-dichloropyridine can be chlorinated to form 2,3,6-trichloropyridine or 2,3,5,6-tetrachloropyridine these reactions were reportedly run in the liquid phase, with reaction times of up to 90 hours, under high pressure using either ultraviolet radiation, different starting materials such as trichloromethyl-chloropyridines, or temperature above 500° C. or a combination of these. And this afforded yields of less than fifty percent and/or mixtures of chlorinated pyridines containing polymerized products. However, the desired products of the present invention can be obtained by chlorinating 2,6-dichloropyridine at atmospheric pressure in the gas phase at temperatures considerably less than 500° C., with residence times of less than ten seconds. This affords high yields (80% or better) of pure 2,3,6-trichloropyridine or 2,3,5,6-tetrachloropyridine, depending upon the exact conditions used, with negligable polymerization. Of great importance is that chlorination in the four-position of the pyridine ring is almost completely avoided.

Thus, in carrying out the process of the present invention, illustratively described with respect to 2,6-dichloropyridine as the starting material, the starting material is added—either in the form of a melt or dissolved in a solvent such as carbon tetrachloride—to an evaporator kept at a temperature of at least 200° C. The vapors leaving the evaporator are directed into the reactor containing the respective catalysts. The evaporation of the reactant in the evaporator may be optionally assisted by adding gaseous nitrogen, chlorine, or hydrogen chloride.

The reactor can be made from any material which stands up to the conditions of the present reaction. The reactor can either be a fixed bed or a fluidized bed. Since the reaction is carried out at elevated temperatures, the reactor must be heated to the desired temperature to initiate the reaction. Once the reaction is underway, the exothermic nature of the reaction requires cooling of the reactor to keep the temperature within the described temperature range.

Chlorine gas is simultaneously passed into the reactor. After passing through the reactor the products and unreacted reactants are collected by cooling and condensation in a collector kept at 0° C. The hydrogen chloride and unreacted chlorine are removed by scrubbing in caustic. Alternatively, they may be optionally separated by known methods and recycled into the reactor. The resultant liquid product is worked up by standard methods to afford high yields of 2,3,5,6-tetrachloropyridine. Any unreacted 2,6-dichloropyridine or intermediate 2,3,6-trichloropyridine can be optionally recycled to produce additional 2,3,5,6-tetrachloropyridine.

The reaction process is generally illustrated below, on a batch-wise basis, for the preparation of 2,3,5,6-tetrachloropyridine.

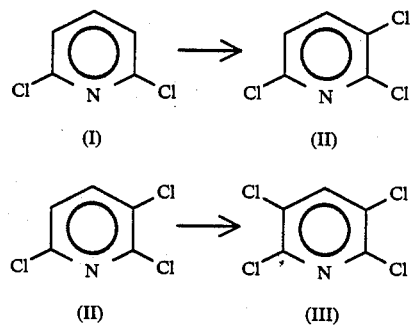

Thus, it has surprisingly been found that the high yields of products (II) and (III) may be obtained in an efficiently short time, depending upon the catalysts and cnditions used. As shown in the above scheme, the reaction follows a step-wise manner. However, those skilled in the art will appreciate that products (II) and (III), can also be obtained as primary products of from reactant (I), and that material (III) can be obtained from a mixture of (I) and (II). The use of any one or more or mixtures of these as starting materials is to be understood as being embodiments within the scope of the present invention.

In a first preferred embodiment of the present invention, the process of the present invention is used to prepare 2,3,5,6-tetrachloropyridine (III) by reacting (I) with a 25-50 percent excess of chlorine using as a catalyst 1-10% activated carbon on attapulgite at a temperature in the range of 300°-450° C., depending upon the residence time.

In a second preferred embodiment, the process of the present invention is selectively practised to obtain optimum amounts of product (II) from (I). This is done most effectively using a 25-50 percent excess of chlorine and zeolite as a catalyst, at a temperature of 250°-320° C.

In a third preferred embodiment of the present invention, the process of the present invention is used to prepare (III) from (II). This is done most efficiently by using a 20-35 percent excess chlorine, 1-10% activated carbon on attapulgite, and a temperature of 350°-450° C., depending upon the residence time.

While the invention will now be described in connection with certain preferred embodiments in the following examples, it will be understood that it is not intended to limit the invention to these particular embodiments. On the contrary it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

The reactor used in this and all further examples consisted of a glass tube having a diameter of 4 cm and a length of 30 cm. It is filled with granuals of the respective catalysts having a diameter of 2-5 mm. The reactor was heated electrically by an external heater; and was attached to an evaporator kept at a temperature of 200°-400° C. Pure reactant is added to the evaporator in the form of a melt or dissolved in a solvent such as carbon tetrachloride in a concentration of 2-98% of reactant. The evaporation can be optionally assisted by adding gaseous nitrogen, chlorine, or hydrogen chloride.

To the above evaporator is added pure 2,6-dichloropyridine at a rate of addition of 1 mole per hour. Simultaneously, 3 moles per hour of chlorine gas is added to the reactor filled with 10% activated carbon on attapulgite and kept at a temperature of 490° C. Using a residence time of 1.0 seconds afforded the following mixture: 12 percent 2,3,6-trichloropyridine, 85 percent 2,3,5,6-tetrachloropyridine, and 3 percent pentachloropyridine.

EXAMPLES 2-19

Following the method of Example 1, 2,3,5,6-tetrachloropyridine was prepared in high yield using a variety of catalysts and reaction conditions. Details and results of Examples 1-19 are shown in Table 1. All results are from a one-pass reaction.

TABLE 1

| | | CHLORINATION OF 2,6-DICHLOROPYRIDINE TO PREPARE 2,3,6-TRICHLOROPYRIDINE AND/OR 2,3,5,6-TETRACHLOROPYRIDINE | | | | | | | | |
|---|---|---|---|---|---|---|---|---|---|---|
| | Form | Rate of Addition[b] | | | | Residence | Mixture Obtained (Percent) | | | |
| Example | of I[a] | I | Chlorine | Temperature[c] | Catalyst[d] | Time[e] | I | II | III | IV[k] |
| 1 | Neat | 1.0 | 3.0 | 490 | AC-10 | 1.0 | — | 12 | 85 | 3 |

TABLE 1-continued

CHLORINATION OF 2,6-DICHLOROPYRIDINE TO PREPARE
2,3,6-TRICHLOROPYRIDINE AND/OR 2,3,5,6-TETRACHLOROPYRIDINE

| Example | Form of I[a] | Rate of Addition[b] I | Chlorine | Temperature[c] | Catalyst[d] | Residence Time[e] | Mixture Obtained (Percent) I | II | III | IV[k] |
|---|---|---|---|---|---|---|---|---|---|---|
| 2 | Neat | 1.0 | 3.0 | 470 | AC-10 | 0.9 | [h] | 31.4 | 66.7 | — |
| 3 | Neat | 1.0 | 3.0 | 410 | AC-10 | 1.0 | — | 14.6 | 82 | 3.2 |
| 4 | Neat | 0.5 | 1.5 | 340 | AC-2 | 3.4 | — | 11.2 | 87.2 | 1.5 |
| 5 | Neat | 1.0 | 3.0 | 400 | AC-2 | 0.8 | — | 32.5 | 65.3 | 2.1 |
| 6 | Neat | 1.0 | 3.0 | 450 | AC-2 | 1.0 | [h] | 9.7 | 82.5 | 5.6 |
| 7 | 10/CTC[f] | 0.15 | 0.44 | 350 | A | 2.4 | — | 24.2 | 73.8 | 2 |
| 8 | 10/CTC | 0.15 | 0.44 | 350 | A | 0.8 | 31.9 | 44.8 | 23 | 0.2 |
| 9 | Neat | 0.5 | 1.5 | 420 | A | 0.7 | — | 20.3 | 76 | 3.6 |
| 10 | Neat | 1.0 | 3.0 | 420 | A | 1.2 | [h] | 56.8 | 39.7 | 0.6 |
| 11 | Neat | 0.5 | 1.5 | 525 | A | 1.3 | [i] | 32.5 | 26.8 | 11.6 |
| 12 | Neat | 0.15 | 0.45[j] | 250 | Kaolin | — | [h] | 28.0 | 70.1 | 0.8 |
| 13 | 2/CTC[g] | 0.006 | 0.052 | 340 | PMF-9 | 3.0 | — | 5.9 | 91.5 | 2.6 |
| 14 | 2/CTC | 0.038 | 0.7 | 360 | CRF-1 | 3.0 | — | 7.0 | 82.3 | 10.7 |
| 15 | 10/CTC | 0.036 | 0.2 | 260 | A | 3.0 | 5.5 | 68 | 26.5 | — |
| 16 | 20/CTC | 0.115 | 0.69 | 500 | A | 3.0 | 15.6 | 50.5 | 32.7 | 1.2 |
| 17 | 2/CTC | 0.038 | 0.7 | 220 | CRF-1 | 3.0 | 15.6 | 63.8 | 16.8 | 4.1 |
| 18 | 2/CTC | 0.04 | 0.2 | 300 | A | 3.0 | — | 15 | 83 | 2 |
| 19 | Neat | 0.2 | 0.7[n] | 300 | B | 5.6 | 14 | 81 | 5.0 | — |

[a]I, II, III as defined in the description
[b]Moles per hour
[c]Degrees Celcius
[d] = attapulgite
AC-2 = 2% C on attapulgite
AC-10 = 10% C on attapulgite
PMF-9 = 9% Fe on a pyrophyllite-bentonite mixture
CRF-1 = 1% Fe on carborundum
B = Baylite WE-894
[e]In seconds
[f]10% I in Carbon tetrachloride
[g]2% I in Carbon tetrachloride
[h]Less than 3% I
[i]7% 2,4,6-trichloropyridine and 19.1% 2,3,4,6-tetrachloropyridine
[j]Also 0.3 mole per hour N$_2$
[k]IV = pentachloropyridine

EXAMPLES 20–23

Following the method of Example 1, but using 2,3,6-trichloropyridine in place of 2,6-dichloropyridine, 2,3,5,6-tetrachlorlopyridine was obtained in high yield using a variety of catalysts and reaction conditions as shown in Table 2.

COMPARATIVE EXAMPLES 24–28

Following the method of Example 1, at attempt was made to chlorinate 2,6-dichloropyridine but using glass rings, carborundum or no filler at all in place of the catalysts of this invention. The results of these comparative examples shown in Table 3, demonstrate that either no reaction takes place or that a great deal of the undesirable 4-chloro-substituted pyridines are formed.

TABLE 2

CHLORINATION OF 2,3,6-TRICHLOROPYRIDINE TO PREPARE 2,3,5,6-TETRACHLOROPYRIDINE

| Example | Form of II[a] | Rate of Addition II | Chlorine | Temperature | Catalyst | Residence Time | Mixture Obtained (Percent) II | III | IV |
|---|---|---|---|---|---|---|---|---|---|
| 20 | 20/CTC | 0.1 | 0.3 | 330 | A | 5.9 | 37.6 | 62.4 | — |
| 21 | 20/CTC | 0.1 | 0.3 | 380 | A | 5.5 | 17 | 81 | 2 |
| 22 | 20/CTC | 0.1 | 0.3 | 300 | AC-2 | 6.0 | 25.3 | 74.2 | — |
| 23 | 20/CTC | 0.1 | 0.3 | 420 | AC-2 | 5.3 | 5.2 | 93.2 | 1.2 |

[a]See Table 1 for key to all abbreviations

TABLE 3

ATTEMPTS TO CHLORINATE 2,6-DICHLOROPYRIDINE WITHOUT USING A CATALYST

| Comparative Example | Form of I[a] | Rate of Addition I | Chlorine | Temperature | Filler | Residence Time | PRODUCT |
|---|---|---|---|---|---|---|---|
| 24 | 2/CTC | 0.01 | 0.28 | 250 | Glass rings | 7.5 | 100% I |
| 25 | 10/CTC | 0.14 | 0.35 | 250 | Carborundum | 4.1 | 100% I |
| 26 | 10/CTC | 0.14 | 0.35 | 450 | Carborundum | 3.0 | 77% I<br>8.6% II<br>14.4% 2,4,6-trichloropyridine |
| 27 | 50/CTC | 0.25 | 1.5 | 420 | None | 3.0 | 74.3% I<br>6.2% II<br>11.7% 2,4,6-trichloropyridine |
| 28 | 50/CTC | 0.25 | 1.5 | 520 | None | 3.0 | 2% I<br>8.1% II<br>30% 2,4,6-trichloropyridine<br>10% III<br>24.6% 2,3,4,6-tetrachloropyridine |

TABLE 3-continued

| ATTEMPTS TO CHLORINATE 2,6-DICHLOROPYRIDINE WITHOUT USING A CATALYST | | | | | | |
|---|---|---|---|---|---|---|
| Comparative Example | Form of I[a] | Rate of Addition I | Chlorine | Temperature | Filler | Residence Time PRODUCT |
| | | | | | | 24.9% IV |

[a]See Table 1 for key to all abbreviations

COMPARATIVE EXAMPLES 29–37

The results from the closest prior art (U.S. Pat. No. 3,420,833 and U.S. Pat. No. 3,370,062) are tabulated in Table 4. The results from U.S. Pat. No. 3,420,833 show either the exclusive formation of pentachloropyridine or the formation of mixtures of pentachloropyridine with significant amounts of the undesireable 2,4,6-trichloropyridine and/or 2,3,4,6-tetrachloropyridine. The results from U.S. Pat. No. 3,370,062 shows again either exclusive formation of pentachloropyridine with no chance to stop attri- or tetrachlorinated pyridines. or the overwhelming formation of a mixture of 2-chloro- and 2,6-dichloropyridines.

TABLE 4

| RESULTS OF REACTING PYRIDINE WITH CHLORINE FROM CLOSEST PRIOR ART | | | |
|---|---|---|---|
| Example | Reference | Temperature | PRODUCTS |
| 29 | U.S. Pat. No. 3,420,833/Ex. 1[a] | 560° C. | Mostly IV[b] |
| 30 | U.S. Pat. No. 3,420,833/Ex 2 | 505° C. | 39% 2,4,6-trichloropyridine |
| | | | 23% 2,3,4,6-tetrachloropyridine |
| | | | 10% 2,3,5,6-tetrachloropyridine |
| 31 | U.S. Pat. No. 3,420,833/Ex. 3 | 525° C. | 75% IV |
| | | | 15% 2,3,4,6-tetrachloropyridine |
| 32 | U.S. Pat. No. 3,420,833/Ex. 4(a) | 480° C. | 42% 2,4,6-trichloropyridine |
| | | | 17% II |
| | | | 5% 2,3,4,6-tetrachloropyridine |
| 33 | U.S. Pat. No. 3,420,833/Ex. 4(b) | 510–520° C. | 31% 2,3,4,6-tetrachloropyridine |
| | | | 30% 2.4.5-trichloropyridine |
| | | | 8% II |
| | | | 24% IV |
| 34 | U.S. Pat. No. 3,370,062/Ex. 1[c] | 300–450° C. | Mostly IV |
| 35 | U.S. Pat. No. 3,370,062/Ex. 2 | 500° C. | Mostly IV (41% yield) |
| 36 | U.S. Pat. No. 3,370,062/Ex. 3 | 500° C. | Mostly IV (50% yield) |
| 37 | U.S. Pat. No. 3,370,062/Ex. 4 | 400° C. | 87% of a mixture containing 2-chloropyridine and I. |
| | | | 13% of a mixture of undefined tri-and tetrachloropyridines |

[a]Residence time of 21 seconds. Residence time not mentioned in other examples of this patent.
[b]See Table 1 for key to all abbreviations.
[c]Residence times of 2–20 seconds.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come with the meaning and range of equivalency of the claims are therefore intended to be embraced therein.

What is claimed is:

1. A process for the selective chlorination of a polychlorinated pyridine chosen from the group consisting of 2,6-dichloropyridine and 2,3,6-trichloropyridine comprising continuously reacting chlorine in the gas phase with at least one of said halopyridines at a temperatures of at least about 200° C. and in the presence of a catalyst selected from the group consisting of silicates, silicate clays, mineral earths, zeolites, diatomaceous earths, carborundum, or mixtures thereof, said diatomaceous earths or carborundum containing an additive selected from the group consisting of activated carbon, iron, zinc, aluminum or a Lewis acid halide, whereby 2,6-dichloropyridine is selectively chlorinated to predominantly form 2,3,6-trichloropyridine, 2,3,5,6-tetrachloropyridine or mixtures thereof, and 2,3,6-trichloropyridine is selectively chlorinated to predominantly form 2,3,5,6-tetrachloropyridine.

2. A process for the selective chlorination of a polychlorinated pyridine chosen from the group consisting of 2,6-dichloropyridine and 2,3,6-trichloropyridine comprising continuously reacting chlorine in the gas phase with at least one of said halopyridines at a temperature of at least about 200° C. and in the presence of a catalyst selected from the group consisting of silicates, silicate clays, mineral earths and zeolites in combination with an additive selected from the group consisting of activated carbon, iron, zinc or a Lewis acid halide, whereby 2,6-dichloropyridine is selectively chlorinated to predominantly form 2,3,6-trichloropyridine, 2,3,5,6-tetrachloropyridine or mixtures thereof, and 2,3,6-trichloropyridine is selectively chlorinated to predominantly form 2,3,5,6-tetrachloropyridine.

3. A process in accordance with claim 1, wherein the catalyst is a silicate.

4. A process in accordance with claim 2, wherein the catalyst is pyrophyllite.

5. A process in accordance with claim 1, wherein the catalyst is selected from the group consisting of attapulgite, sepiolite, bentonite, saponite, hectonite, or kaolinite.

6. A process in accordance with claim 1, wherein the catalyst is attapulgite.

7. A process in accordance with claim 1, wherein the catalyst is bentonite.

8. A process in accordance with claim 1, wherein the catalyst is kaolin.

9. A process in accordance with claim 1, wherein the catalyst is a zeolite.

10. A process in accordance with claim 1, wherein the catalyst is activated carbon on an alkali metal silicate clay.

11. A process in accordance with claim 1, wherein the catalyst is activated carbon on attapulgite.

12. A process in accordance with claim 11, wherein the catalyst contains activated carbon in a weight ratio of from 1 to 25 percent.

13. A process in accordance with claim 12, wherein the catalyst contains activated carbon in a weight ratio of from 1 to 25 percent.

14. A process in accordance with claim 1, wherein the Lewis acid halide is ferric chloride.

15. A process in accordance with claim 1, wherein the catalyst is ferric chloride on a pyrophyllite-bentonite mixture.

16. A process in accordance with claim 14 wherein the catalyst is ferric chloride on carborundum.

17. A process in accordance with claim 16 wherein the ferric chloride is present in a weight ratio of from 1 to 10 percent.

18. A process in accordance with claim 1 wherein the catalyst is a mixture of two or more of these catalysts.

19. A process in accordance with claim 18 wherein the mixed catalyst contains pyrophyllite and bentonite.

20. A process in accordance with claim 19 wherein the mixed catalyst contains pyrophyllite and bentonite in a weight ratio of from 1:10 to 1:5.

21. A process in accordance with claim 20 wherein the pyrophyllite and bentonite are mixed in a weight ratio of from 1:9 to 1:7.

22. A process in accordance with claim 1 wherein the reaction is carried out without any solvent.

23. A process in accordance with claim 1 wherein the reaction is carried out in the presence of an inert solvent.

24. A process in accordance with claim 23 wherein the solvent is a halogenated hydrocarbon.

25. A process in accordance with claim 24 wherein the solvent is carbon tetrachloride.

26. A process in accordance with claim 1 wherein the mole ratio of chloropyridine reactant to chlorine is from 1:1 to 1:25.

27. A process in accordance with claim 26 wherein the mole ratio of chloropyridine reactant to chlorine is from 1:3 to 1:20.

28. A process in accordance with claim 1 wherein the reaction temperature is in the range from 200° C. to 500° C.

29. A process in accordance with claim 1 wherein the residence time of the mixture in the reaction zone is between 0.1 and 20 seconds.

30. A process in accordance with claim 29 wherein the residence time of the mixture in the reaction zone is between 0.5 and 6 seconds.

31. A process for preparing 2,3,6-trichloropyridine and 2,3,5,6-tetrachloropyridine comprising continuously reacting chlorine with 2,6-dichloropyridine in the gas phase in a mole ratio of from 20:1 to 3:1 at a temperature between 200° and 500° C. characterized in that the reaction is conducted in the presence of a catalyst selected from the group consisting of attapulgite, kaolin, zeolites, activated carbon on attapulgite, ferric chloride on a pyrophyllite bentonite mixture, and ferric chloride on carborundum.

32. A process in accordance with claim 31 wherein the activated carbon is present in a weight ratio of from 1 to 15 percent.

33. A process in accordance with claim 31 wherein the ferric chloride is present in a weight ratio of from 1 to 10 percent.

34. A process in accordance with claim 31 wherein the pyrophyllite and bentonite are mixed in a weight ratio of from 1 to 10.

35. A process in accordance with claim 31 wherein the reaction is carried out without any solvent.

36. A process in accordance with claim 31 wherein the reaction is carried out in the presence of carbon tetrachloride as a solvent.

37. A process for preparing 2,3,5,6-tetrachloropyridine comprising continuously reacting chlorine with 2,3,6-trichloropyridine in the gas phase in a mole ratio of from 3 to 1 at a temperature between 300° C. and 450° C. characterized in that the reaction is conducted in the presence of a catalyst selected from the group consisting of attapulgite and activated carbon on attapulgite.

38. A process in accordance with claim 37 wherein the activated carbon is present in a weight ratio of from 1 to 15 percent.

39. A process in accordance with claim 37 wherein the reaction is carried out without any solvent.

40. A process in accordance with claim 37 wherein the reaction is carried out in the presence of carbon tetrachloride as a solvent.

* * * * *

UNITED STATES PATENT AND TRADEMARK OFFICE
CERTIFICATE OF CORRECTION

PATENT NO. : 4,810,797
DATED : March 7, 1989
INVENTOR(S) : SHARVIT et al.

It is certified that error appears in the above-identified patent and that said Letters Patent is hereby corrected as shown below:

Column 1, line 55    Delete "2-chlorpyridine", insert therefor
                     -- 2-chloropyridine --

Column 3, line 52    Delete " montmorrilloniod", insert therefor
                     -- montmorrillonite --

Column 3, line 53    Delete "hectories", insert therefor
                     -- hectorites --

Column 4, line 1     Delete "ddited", insert therefor
                     -- edited --

Column 4, line 26    Delete "diatamaceous", insert therefor
                     -- diatomaceous --

Column 7, table 1    In footnote d, before "=", insert -- A --

Column 9, line 20    Delete "attri-", insert therefor
                     -- at tri- --

UNITED STATES PATENT AND TRADEMARK OFFICE
CERTIFICATE OF CORRECTION

PATENT NO. : 4,810,797

DATED : March 7, 1989

INVENTOR(S) : SHARVIT et al.

It is certified that error appears in the above-identified patent and that said Letters Patent is hereby corrected as shown below:

Column 10, line 59    Delete "hectonite", insert therefor -- hectorite --

Signed and Sealed this

Twentieth Day of August, 1991

Attest:

HARRY F. MANBECK, JR.

*Attesting Officer*    *Commissioner of Patents and Trademarks*